United States Patent

Segot et al.

[11] Patent Number: 6,015,568
[45] Date of Patent: Jan. 18, 2000

[54] ANHYDROUS STABLE RETINOL BASED COSMETIC OR PHARMACEUTICAL COMPOSITION

[75] Inventors: Evelyne Segot, Nogent sur Morne; Jean-Pierre Laugier, Antony, both of France

[73] Assignee: L'Oreal, Paris, France

[21] Appl. No.: 08/627,480

[22] Filed: Apr. 4, 1996

Related U.S. Application Data

[63] Continuation of application No. 08/317,879, Oct. 4, 1994, abandoned.

[30] Foreign Application Priority Data

Oct. 5, 1993 [FR] France ................................. 93 11850

[51] Int. Cl.$^7$ ..................................................... A61K 7/00
[52] U.S. Cl. ......................... 424/401; 514/844; 514/845; 514/969
[58] Field of Search ............................. 424/401; 514/844, 514/845, 969

[56] References Cited

U.S. PATENT DOCUMENTS

| | | | |
|---|---|---|---|
| 3,584,115 | 6/1971 | Gebhart et al. | 424/45 |
| 3,622,668 | 11/1971 | Moss | 424/237 |
| 4,022,913 | 5/1977 | Newmark | 424/344 |
| 4,727,088 | 2/1988 | Scott et al. | 514/725 |
| 4,826,828 | 5/1989 | Wilmott | 514/63 |
| 4,826,871 | 5/1989 | Gressel et al. | 514/438 |
| 4,871,723 | 10/1989 | Makino et al. | 514/167 |
| 4,888,363 | 12/1989 | Dulak et al. | 514/725 |
| 4,966,773 | 10/1990 | Gressel et al. | 424/489 |
| 5,002,760 | 3/1991 | Katzev | 424/59 |
| 5,401,517 | 3/1995 | Meyers | 424/401 |
| 5,492,894 | 2/1996 | Bascom | 514/18 |

FOREIGN PATENT DOCUMENTS

| | | |
|---|---|---|
| 0129003 | 12/1984 | European Pat. Off. . |
| 2515034 | 4/1983 | France . |
| 1935939 | 2/1971 | Germany . |
| 51-012591 | 4/1976 | Japan . |
| 1126289 | 9/1968 | United Kingdom . |

OTHER PUBLICATIONS

Chemical Abstracts, vol. 85, No. 83131x.

*Primary Examiner*—Thurman K. Page
*Assistant Examiner*—Alysia Berman
*Attorney, Agent, or Firm*—Nixon & Vanderhye P.C.

[57] ABSTRACT

Anhydrous, stable retinol-based cosmetic or pharmaceutical composition for the skin. This composition contains solubilized retinol in an organic solution which is liquid at ambient temperature and which is chosen from the group comprising:

i) aliphatic fatty alcohols having a branched chain at $C_{16}$–$C_{20}$, ii) saturated alcoxylated fatty alcohols having a straight or branched chain at $C_{16}$–$C_{20}$, iii) the diesters of dicarboxylic esters at $C_6$–$C_{14}$ and of isopropyl alcohol, and mixtures of these solvents.

This composition is intended for the treatment of skin disorders, and of acne in particular.

7 Claims, No Drawings

ANHYDROUS STABLE RETINOL BASED COSMETIC OR PHARMACEUTICAL COMPOSITION

This is a continuation of application Ser. No. 08/317,879, filed Oct. 4, 1994, now abandoned.

The present invention relates to an anhydrous, stable retinol- or vitamin A-based cosmetic or pharmaceutical composition for the skin and to the use thereof for the treatment of skin disorders, in particular for the treatment of acne, keratinization or scarring problems, light-related aging, and the prevention and softening of wrinkles.

Retinol has previously been recommended in the treatment of these disorders: for example, in European Patent Application No. 224,504, which describes a stable composition containing retinol, a volatile silicone, and a solvent of the retinol and volatile silicone.

The solvent used is preferably ethanol. However, studies of this type of composition revealed that retinol decomposed in the presence of ethanol.

An anhydrous cosmetic composition containing retinol as the topical active ingredient has also been disclosed in European Patent Application No. 255,364. In addition to the retinol, this composition also incorporates a liquid emollient, a thickening agent, and a solubilizing agent, as well as anti-oxidants and other preservatives.

It has now been discovered, both unexpectedly and surprisingly, that, by making a determinate selection of solvents not mixable with water to be used as the retinol carrier, it was possible to produce anhydrous compositions intended for topical application and exhibiting a high degree of stability over time, without utilizing anti-oxidants.

Accordingly, the present invention concerns an anhydrous, stable retinol-based cosmetic or pharmaceutical composition for the skin, characterized by the fact that it contains solubilized retinol in an organic solvent which is liquid at ambient temperature and is chosen from the group including:

i) a branched aliphatic fatty alcohol having $C_{16}$–$C_{20}$
  ii) a straight or branched saturated alcoxylated fatty alcohol having $C_{16}$–$C_{20}$
  iii) a diester of dicarboxylic acid having $C_6$–$C_{14}$ and isopropyl alcohol and mixtures of these solvents.

Through the specific selection of solvents, the composition according to the invention proves especially stable over time. No significant decomposition of retinol is observed even in the absence of any additive, in particular of anti-oxidants.

The preservation trials conducted did, indeed, show that, in comparison with other widely-used solvents as a carrier of the active substance, those selected according to the present invention yielded clearly-improved stability.

The aliphatic fatty alcohols having a branched chain at $C_{16}$–$C_{20}$ that can be used according to the invention are preferably saturated. These products include isostearyl alcohol, such as that sold by the Sherex Company under the name ADOL 66, 2-hexyl decanol, such as that sold by the Condea Company under the name ISOFOL 16 and octyl dodecanol such as that sold by the Henkel Company under the name EUTANOL G.

Among the saturated alcoxylated fatty alcohols having a straight or branched chain at $C_{16}$–$C_{20}$ that can be used according to the invention, preference is given to those containing 10 to 50 moles of ethylene oxide and/or propylene oxide.

Among the latter, mention may be made, in particular, of stearyl alcohol into which propylene oxide has been incorporated using 15 moles propylene oxide, such as the product sold by the ICI company under the name ARLAMOL E.

Among the diesters of dicarboxylic acids at $C_6$–$C_{14}$ and of isopropyl alcohol that can be used according to the invention, mention may be made of diisopropyl adipate, such as the product sold by the ISP Company under the name CERAPHYL 230.

The composition according to the invention as specified above may be used in that form in the localized treatment of skin disorders, as well as in anti-aging treatments.

In general, retinol is incorporated into the composition according to the invention in a proportion of between 0.001 and 15%, and preferably between 0.01 and 10% by weight of the total weight of the composition, the remainder being composed essentially of the organic solvent liquid at ambient temperature, as described above.

Some customarily-used ingredients may be added to the composition according to the invention, as is conventionally done for anhydrous cosmetic or pharmaceutical compositions, to the extent that these ingredients are soluble and do not modify the stability thereof.

However, according to a preferred embodiment, the composition according to the invention is produced in a form intended for topical application, as, for example, a lotion composed solely of retinol in solution in at least one of the organic solvents previously specified.

The present invention also relates to a composition packaged in two parts, the first part being composed of a solution of retinol in one of the organic solvents mentioned above, and the second part being composed of a conventional cosmetic or pharmaceutical medium existing, for example, as a gel, an emulsion, or an ointment, the two parts being mixed at the time of use and causing formation of a lotion.

In addition to a gelling or emulsifying agent, the cosmetic or pharmaceutical medium may further contain various additives, such as filters, perfumes, dyes, or fillers.

STUDY OF STABILITY

This study was intended to examine the stability of retinol when combined with various solvents over time and as a function of temperature.

Given the sensitivity of retinol to air, light, and heat, certain conditions governing the preparation of the samples were adhered to. Accordingly, all handling was done in a darkened room in inactinic light and under nitrogen. The various solvents were preliminarily deoxygenized by nitrogen bubbling; next, the retinol was solubilized by magnetic stirring at ambient temperature. For each solvent, two compositions were tested in 10% retinol/solvent ratios by weight. The samples were then packaged under nitrogen in brown glass bottles protected from light. These bottles were then stored at 4° C., at ambient temperature (AT), at 37° C., and at 45° C. for two months.

Following this storage time, quantitative analyses were performed using the technique of high performance liquid chromatography (HPLC) under the following conditions:

| | |
|---|---|
| Column: | 2 15-cm columns, diameter = 4 mm<br>Spherisorb ODS1 5 μm<br>Alltech ODS1 |
| Eluant: | solvent gradient |
| Solvent A: | acetonitrile = 850 ml<br>anhydrous ammonium acetate = 400 mg<br>100% acetic acid = 10 ml<br>water = 140 ml |
| Solvent B: | acetonitrile = 60 ml |

-continued

|  | isopropanol = 40 ml | | |
|---|---|---|---|
| Gradient: | Time (mn.) | A (%) | B(%) |
|  | 0 | 100 | — |
|  | 20 | 100 | — |
|  | 25 | — | 100 |
|  | 35 | — | 100 |
|  | 40 | 100 | — |
|  | 50 | 100 | — |

| Flow Rate: | 1 ml/mn |
|---|---|
| Detection: | UV spectrophotometry at 340 nm |
| Adjustment range and sample: | Preparation of a range of ethanol-containing retinol solutions of from 25 to 100 μg/ml - 10 μl injection. Preparation of samples - dilution in ethanol. |

The results, which correspond to the average of three measurements, are expressed in terms of the percentage of decomposed retinol after storage for two months under the conditions described above. The values obtained for each solvent are given in Table 1 below:

TABLE 1

| Temperatures | +4° C. | AT | 37° C. | 45° C. |
|---|---|---|---|---|
| Propylene glycol | −25 | −34 | −65 | −84 |
| Ethanol | 0 | −3 | −6 | −21 |
| Stearyl alcohol incorporating propylene oxide using 15 moles of propylene oxide | 0 | 0 | 0 | −9 |
| Isostearyl alcohol | 0 | 0 | 0 | −8 |
| 2-hexyl decanol | 0 | 0 | 0 | 0 |
| Octyl dodecanol | 0 | 0 | 0 | 0 |
| Diisopropyl adipate | 0 | 0 | 0 | 0 |

We will now provide as illustrations several examples of the retinol-based composition according to the invention. These compositions were prepared in the same manner as that implemented for the stability study described above.

COMPOSITION EXAMPLES

| Example 1: Topical lotion | |
|---|---|
| stearyl alcohol in which propylene oxide was incorporated using 15 moles propylene oxide | 90% |
| retinol | 10% |
| Example 2: Topical lotion | |
| octyl dodecanol | 90% |
| retinol | 10% |
| Example 3: Topical lotion | |
| 2-hexyl decanol | 91% |
| retinol | 9% |

When applied once per week on the affected skin areas, the lotions in Examples 1 to 3 above prevent and soften the formation of wrinkles.

| Example 4: Composition packaged in two parts for preparation of a lotion | |
|---|---|
| At the time of use, Part A, below: | |
| Part A: | |
| diisopropyl adipate | 9.5 grams |
| retinol | 0.5 gram |
| is mixed with Part B, below: | |
| Part B: | |
| xanthane gum | 0.7 gram |
| preservative | 0.3 gram |
| water | 89.0 grams |

A milky, gelled product is produced, which is applied to the acne-afflicted areas of the skin requiring treatment. After application twice weekly for about 4 to 5 weeks, a reduction of the acne-stricken areas is noted.

This same composition applied on healthy skin prevents and softens wrinkles.

We claim:

1. An anhydrous retinol based cosmetic lotion consisting of a cosmetically or pharmaceutically effective amount of retinol solubilized in an organic solvent liquid at ambient temperature, said organic solvent being selected from the group consisting of:

(i) a branched aliphatic alcohol having $C_{16}$–$C_{20}$, (ii) a straight or branched saturated alkyoxylated fatty alcohol having $C_{16}$–$C_{20}$, and a mixture thereof.

2. The anhydrous retinol based lotion of claim 1 wherein said retinol is present in a proportion of between 0.01 and 10 percent relative to the total weight of said composition.

3. The anhydrous retinol based lotion of claim 1 wherein said branched aliphatic fatty alcohol having $C_{16}$–$C_{20}$ is selected from the group consisting of isostearyl alcohol, 2-hexyl decanol and octyl dodecanol.

4. The anhydrous retinol based lotion of claim 1 wherein said straight or branched saturated alkoxylated fatty alcohol is stearyl alcohol incorporating 15 moles of propylene oxide.

5. The anhydrous retinol based lotion of claim 1 wherein said composition contains no anti-oxidant.

6. A method of making a retinol based cosmetic or pharmaceutical lotion comprising at the time of use the step of mixing a first part packaging composed of a composition of claim 1 with a second part packaging composed of a cosmetically or pharmaceutically acceptable medium selected from the group consisting of a gel, an emulsion and an ointment.

7. The anhydrous retinol based lotion of claim 1 wherein said organic solvent is a $C_{16}$ branched aliphatic alcohol.

* * * * *